US00PP34466P2

(12) United States Plant Patent
Subramanian et al.

(10) Patent No.: US PP34,466 P2
(45) Date of Patent: Aug. 2, 2022

(54) CHERRY TREE NAMED 'V84031'

(50) Latin Name: *Prunus avium*
Varietal Denomination: 'V84031'

(71) Applicant: The University of Guelph, Guelph (CA)

(72) Inventors: Jayasankar Subramanian, Guelph (CA); Bill Lay; Ghassem Tehrani

(73) Assignee: The University of Guelph, Guelph (CA)

( * ) Notice: Subject to any disclaimer, the term of this patent is extended or adjusted under 35 U.S.C. 154(b) by 0 days.

(21) Appl. No.: 17/300,064

(22) Filed: Feb. 24, 2021

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/085
See application file for complete search history.

(56) References Cited

PUBLICATIONS

PLUTO UPOVROM Database Citation for 'V84031' as per CA PBR 10-7088; Feb. 1, 2011; 1 page.*

* cited by examiner

*Primary Examiner* — Kent L Bell
(74) *Attorney, Agent, or Firm* — Michelle Bos Legal LLC

(57) ABSTRACT

'V84031' is a self-fruitful sweet cherry tree distinguished by its early flowering and large mahogany-colored fruit.

6 Drawing Sheets

Genus and species: *Prunus avium.*
Variety denomination: 'V84031'.

BACKGROUND AND SUMMARY OF THE VARIETY

The new sweet cherry variety 'V84031' originated as a single selection from the progeny of a self-pollination of the variety 'Vandalay' (not patented) made in 1984 at Vineland Station, Ontario, Canada. The new variety was selected for further evaluation and propagated by shoot cuttings in 1992 at Vineland Station. 'V84031' was selected for its early fruiting and its tendency to hang on the tree even after edible ripeness, which is conducive to staggered pickings.

'V84031' has been compared to and can be distinguished from parent variety 'Vandalay' and related variety 'Viva' (not patented). The plants of 'V84031' are self-fruitful whereas those of both reference varieties require cross pollination with other varieties to bear fruit. The plants of 'V84031' flower early in the season whereas those of 'Vandalay' flower very early and those of 'Viva' flower late. The petals of 'V84031' are broad obovate whereas those of 'Viva' are circular. The arrangement of the petals of 'V84031' are free whereas those of both reference varieties are intermediate between free and overlapping. The fruit of 'V84031' is large to very large whereas that of 'Viva' is medium to large. The fruit skin of 'V84031' is mahogany whereas the skin of 'Viva' is wine red. The fruit flesh of 'V84031' is black red whereas the flesh of 'Viva' is red.

'V84031' cherry has been found to exhibit its distinctive characteristics through successive asexually propagated generations.

BRIEF DESCRIPTION OF THE PHOTOGRAPHS

The accompanying photographs were obtained at Vineland Station in 2013.

Figure 1:
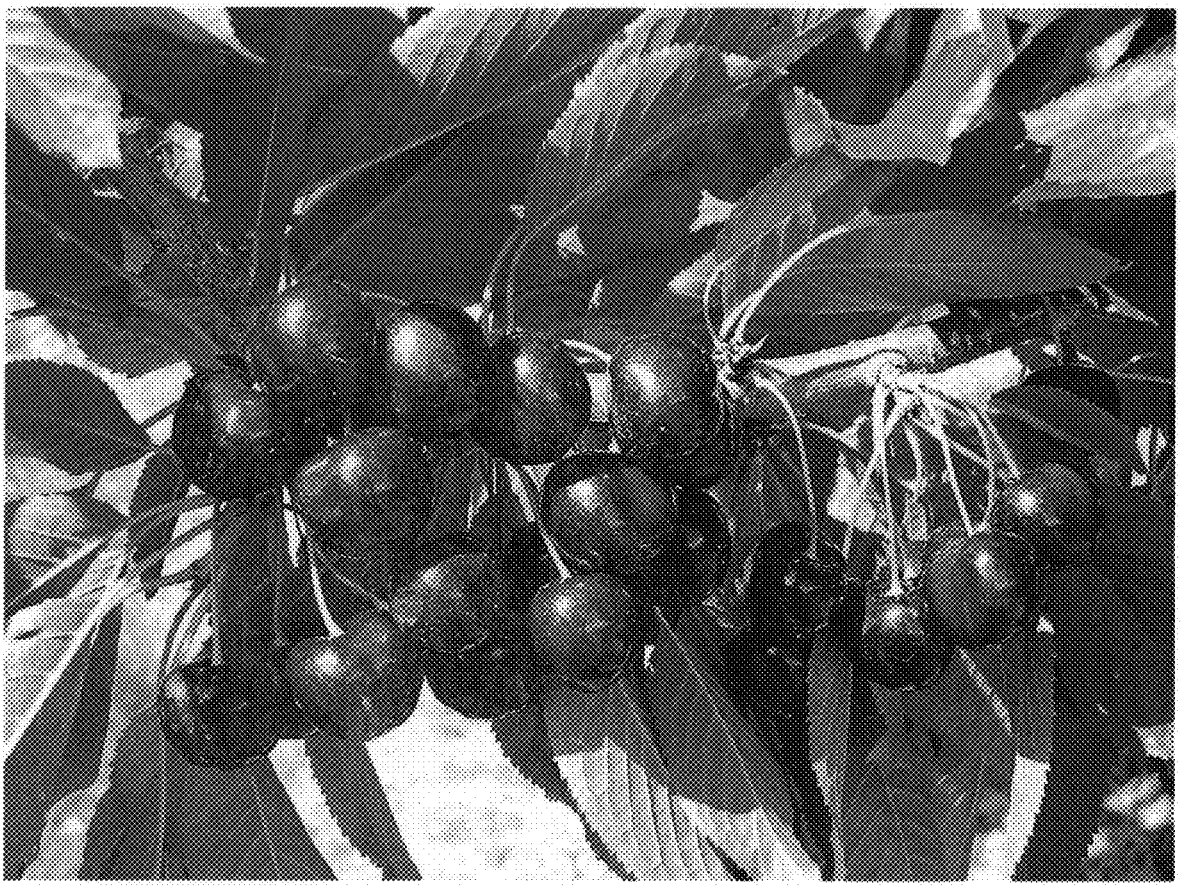
FIG. 1 shows the fruit and leaves of 'V84031'.
Figure 2:
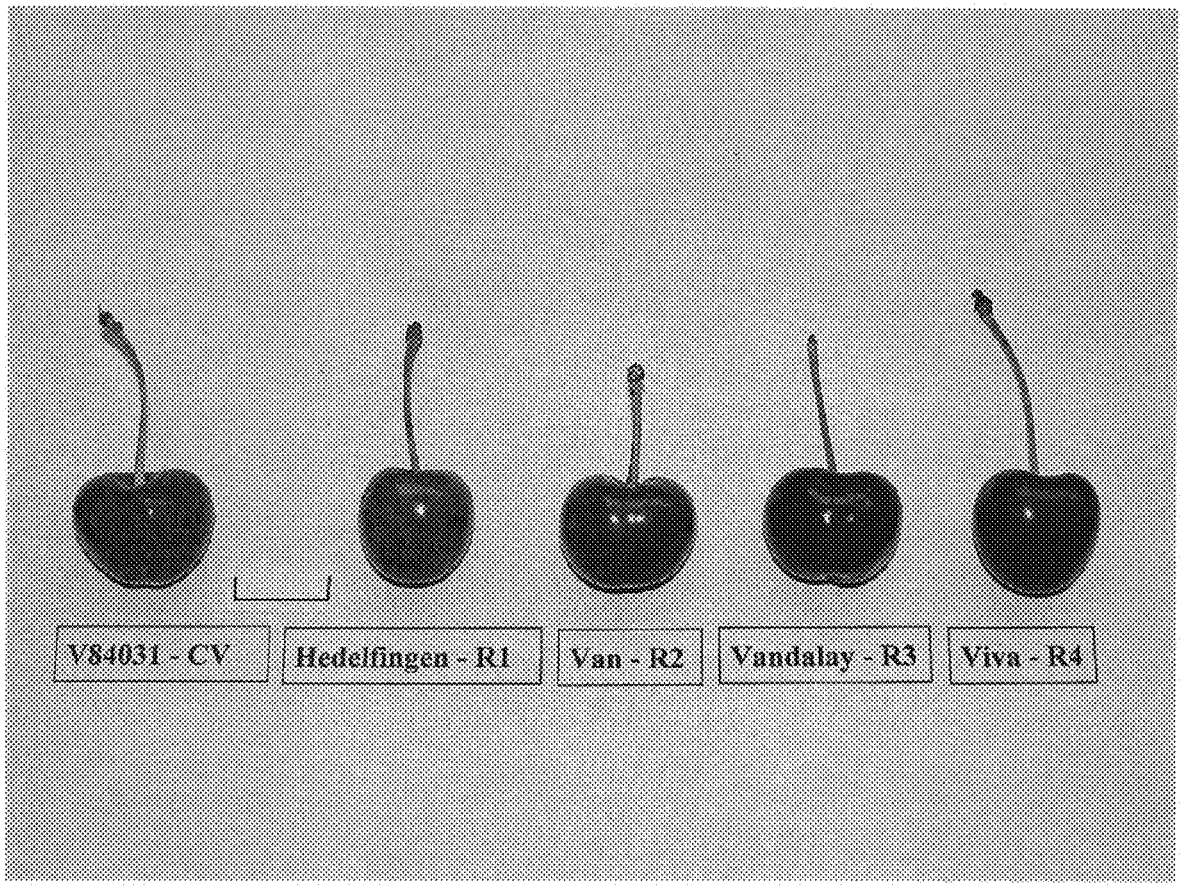
FIG. 2 shows whole fruits of 'V84031' and comparison varieties.
Figure 3:
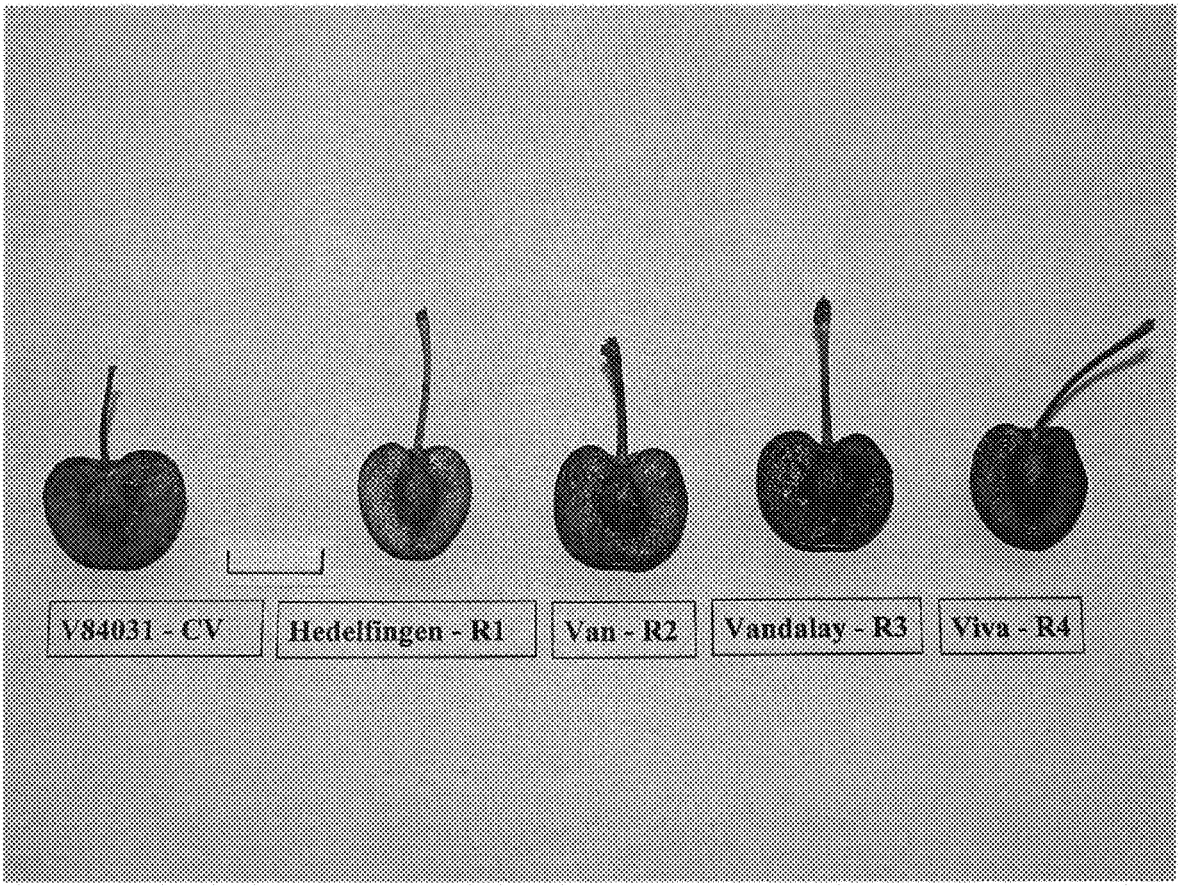
FIG. 3 shows sectioned fruits of 'V84031' and comparison varieties.
Figure 4:
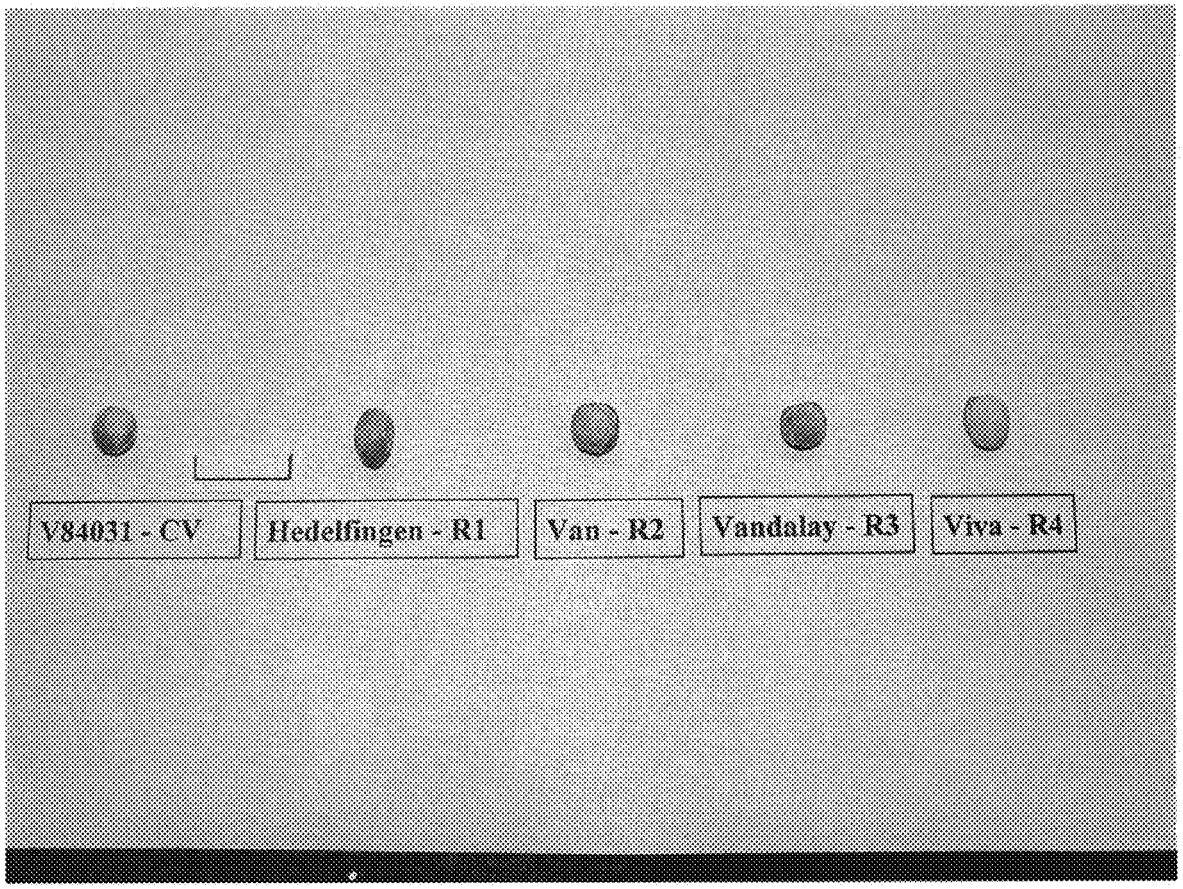
FIG. 4 shows stones of 'V84031' and comparison varieties.
Figure 5:
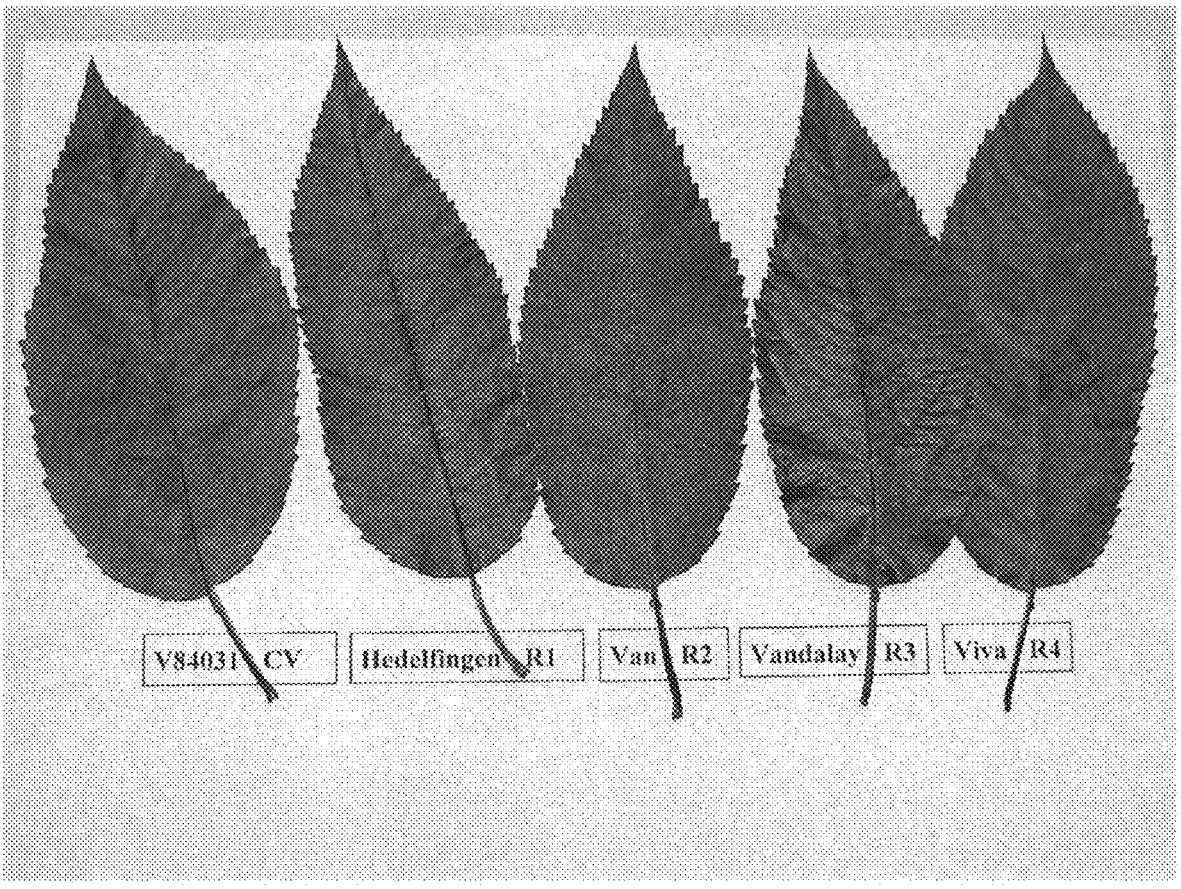
FIG. 5 shows leaves of 'V84031' and comparison varieties.
Figure 6:
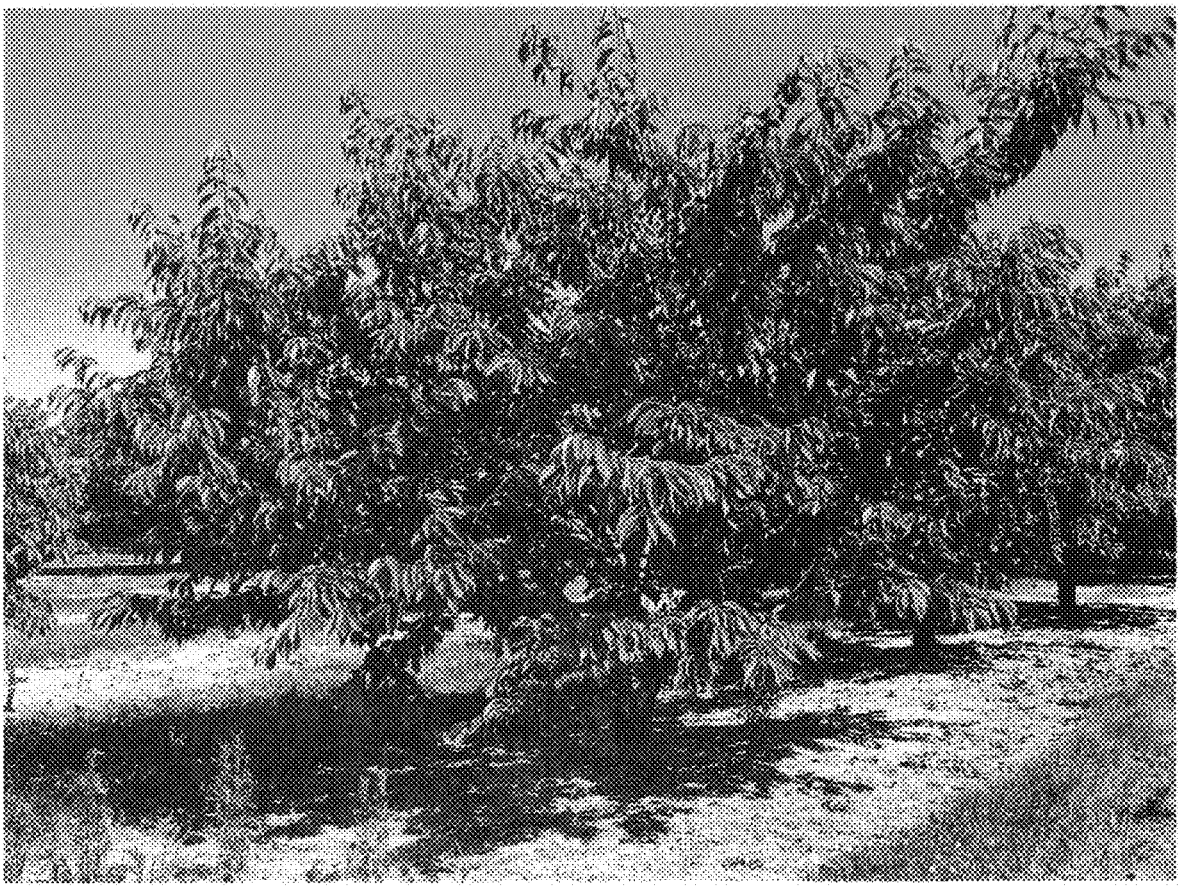
FIG. 6 shows a 17-year-old tree of 'V84031'.

The colors shown in these photographs may vary with lighting conditions. Color characteristics of the claimed variety should therefore be determined with reference to the observations described herein, rather than from the photographs alone.

DETAILED BOTANICAL DESCRIPTION

The following detailed botanical description is based on observations made at Vineland Station in 2013 of second-generation trees of the variety planted in 1997. Additional observations were recorded near Wapato, Wash. during the 2021 growing season of 7-year-old trees grown on Maxma® rootstock. The characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Color descriptions are made with reference to The RHS Colour Chart (Royal Horticultural Society, 2001).

Tree:
*Vigor.*—Moderate vigor.
*Habit, shape.*—Spreading.
*Density.*—Medium to dense.
*Height* (7-*year-old tree*).—About 3 m.
*Spread* (7-*year-old tree*).—About 1.4 m.
*Trunk diameter at* 30 *cm above graft.*—13.5 cm.
*Bark texture.*—Rough.
*Bark color.*—Greyed-purple 183B with grey 201D overcolor.

Mature branches:
*Length.*—100 cm.
*Diameter.*—2 cm.
*Crotch angle.*—Upwards, about 100 degrees.
*Bark color.*—Greyed-purple 183B.
*Bark texture.*—Rough.

One year old shoot:
*Length.*—32 cm.
*Diameter.*—1 cm.
*Color.*—Greyed-purple 183B.
*Attitude.*—Erect to horizontal.
*Internode length.*—Medium, 6 cm to 10 cm.
*Pubescence.*—Absent or very weak.
*Lenticel quantity.*—Medium to many, 20 or more per 10 cm length.
*Lenticel diameter.*—2 mm.
*Lenticel color.*—Grey 201D.
*Number of flower buds.*—Absent or very few.
*Vegetative bud size.*—Small to medium; length 2 cm to 3 cm; diameter 0.5 cm to 0.7 cm.
*Vegetative bud shape.*—Ovate.
*Vegetative bud position in relation to shoot.*—Clearly held out.
*Size of vegetative bud support.*—Medium to large.

Current year shoot:
*Length.*—35 cm to 40 cm.
*Diameter.*—0.8 cm to 1.2 cm.
*Internode length.*—6 cm to 8 cm.
*Color.*—Light green 144C.
*Pubescence.*—Absent or very weak.
*Anthocyanin coloration at tip.*—Medium to strong.

Leaves:
*Attitude in relation to shoot.*—Horizontal.
*Shape.*—Broad elliptical.
*Angle of tip.*—Right or almost right.
*Shape of base.*—Acute.
*Shape of apex.*—Acuminate.
*Shape of profile.*—Concave to flat.
*Pubescence on lower side.*—Weak.
*Length.*—11.8 cm.
*Width.*—5.8 cm.
*Ratio of length/width.*—2.0:1.
*Color of upper surface.*—Yellow-green 144A.
*Glossiness of upper surface.*—Weak.
*Color of lower surface.*—Yellow-green 144B.
*Margin.*—Biserrate.
*Depth of indentation of margin.*—Shallow.

Petiole:
*Length.*—5.0 cm.
*Diameter.*—1.0 mm.
*Ratio of length of petiole/blade.*—2.4:1.
*Color.*—Yellow-green 144C with some greyed-purple 184C anthocyanin coloration present.
*Number of glands.*—Usually 2.
*Gland length.*—About 2 mm.
*Gland width.*—About 1 mm.
*Gland color.*—Red 50B.
*Gland shape.*—Kidney-shaped.

Flower:
*Flower density.*—Medium to dense, 8 to 12 per cluster.
*Appearance.*—In clusters.
*Type.*—Single.
*Color of bud just prior to bloom.*—White NN155D.
*Bud shape.*—Ovate.
*Bud length.*—7 mm.
*Bud diameter.*—8 mm.
*Diameter.*—21 mm.
*Pedicel length.*—24 mm.
*Pedicel diameter.*—Thin to medium, 2 mm.
*Pedicel color.*—Yellow-green N144B.
*Pedicel pubescence.*—Absent or very weak.
*Petal quantity.*—5 per flower.
*Frequency of flowers with extra petals.*—Absent or very low.
*Petal length.*—Small, 12 mm.
*Petal width.*—Small, 10 mm.
*Petal shape.*—Elliptic.
*Petal apex.*—Rounded.
*Petal base.*—Rounded.
*Petal margin.*—Entire.
*Petal texture.*—Both surfaces smooth.
*Relative position of petal margins.*—Free.
*Color of petal upper side.*—White 155A.
*Color of petal lower side.*—White 155C.
*Color of petal upper side when faded.*—White 155C.

Sepals:
*Quantity.*—5 per flower.
*Color.*—Both surfaces yellow-green 145C.
*Length.*—6 mm.
*Width at base.*—4 mm.
*Shape.*—Triangular.
*Apex.*—Pointed.
*Margin.*—Entire.
*Texture.*—Both surfaces smooth.

Stamen:
*Quantity.*—About 15 per flower.
*Filament length.*—6 mm.
*Filament color.*—White N155B.
*Anther length.*—1 mm.
*Anther shape.*—Oval.
*Color just before dehiscence.*—Yellow.
*Pollen.*—Present, moderately abundant.
*Pollen color.*—Red-purple 59B.

Pistil:
*Presence.*—Present, complete.
*Quantity per flower.*—1.
*Frequency of supplementary pistil.*—Absent or very low.
*Pubescence of ovary.*—Absent.
*Stigma diameter.*—1 mm.
*Stigma color.*—Red-purple 59B.
*Style length.*—3 mm.
*Style color.*—White N155B.
*Ovary length.*—5 mm.
*Ovary color.*—Yellow-green N144A.

Fruit:
*Size.*—Large.
*Axial diameter.*—25 mm.
*Apical diameter.*—25 mm.
*Average weight.*—9.9 g.

*Shape.*—Reniform.
*Profile in lateral view.*—Obovate.
*Position of largest diameter.*—Toward middle.
*Number of light colored dots on skin.*—Few to medium.
*Size of light colored dots on skin.*—Small.
*Color of skin.*—Red 45B with red-purple 59A overcolor.
*Prominence of suture.*—Medium.
*Skin thickness.*—Medium.
*Juice color.*—Red 46A.
*Flesh color.*—Red 46B.
*Flesh texture.*—Fine, melting.
*Firmness.*—Firm.
*Acidity.*—Medium.
*Sweetness.*—Medium to high, 16 to 19 Brix.
*Juiciness.*—Medium.
*Aroma.*—Typical of sweet cherry.
*Apex shape.*—Flat.
*Susceptibility to rain-induced cracking.*—Low.
*Stalk length.*—42 mm to 45 mm.
*Stalk diameter.*—1.5 mm.
*Stalk color.*—Yellow-green 144A.
*Adherence of stalk to fruit.*—Strong.
*Adherence of stalk to spur.*—Weak, releases easily.
*Stalk cavity depth.*—4 mm.
*Stalk cavity diameter.*—13 mm.

Stone:
*Adherence to flesh.*—Free to semi-adherent.
*Length.*—12 mm.
*Diameter.*—8 mm.
*Size relative to fruit.*—Small.
*Shape in lateral view.*—Spherical.
*Shape in front view.*—Elliptic.
*Shape in basal view.*—Round elliptical.
*Symmetry in lateral view.*—Symmetrical.
*Development of keel in lateral view.*—Strong.
*Color.*—Greyed-yellow 161C.
*Texture.*—Smooth, typical of sweet cherry.
*Tendency to split.*—None.

Flowering, fruiting and maturity characteristics:
*Precocity of fruit bearing.*—Intermediate to high.
*Time of leaf bud burst in relation to beginning of full flowering.*—Earlier.
*Time of flowering.*—Early (Apr. 10, 2021 at Wapato, Wash.).
*Fertility.*—Self-fertile.
*Time of fruit maturity.*—Early (Jun. 2, 2021 at Wapato, Wash.).
*Number of picks.*—One.
*Harvest yield.*—35 kg to 40 kg per tree.
*Fruit setting.*—Medium-high to high.
*USDA Hardiness Zone.*—6a.

Reaction to pests and diseases: Moderately resistant to brown rot, blossom and spur blight (*Sclerotinia* spp.); moderately resistant to aphids (*Myzus cerasi* etc.) and bacterial canker (*Pseudomonas* spp.); moderately susceptible to cherry fruit fly (*Rhagoletis* spp.).

The invention claimed is:

1. A new and distinct variety of cherry tree named 'V84031', substantially as illustrated and described herein.

* * * * *